(12) United States Patent
Plojoux et al.

(10) Patent No.: US 9,854,844 B2
(45) Date of Patent: *Jan. 2, 2018

(54) POLYGONAL AEROSOL-GENERATING DEVICE AND SYSTEM

(71) Applicant: Philip Morris Products S.A., Neuchatel (CH)

(72) Inventors: Julien Plojoux, Geneva (CH); Dani Ruscio, Cressier (CH)

(73) Assignee: Philip Morris Products S.A., Neuchatel (CH)

( * ) Notice: Subject to any disclaimer, the term of this patent is extended or adjusted under 35 U.S.C. 154(b) by 346 days.

This patent is subject to a terminal disclaimer.

(21) Appl. No.: 14/370,333

(22) PCT Filed: Dec. 28, 2012

(86) PCT No.: PCT/EP2012/077090
§ 371 (c)(1),
(2) Date: Jul. 2, 2014

(87) PCT Pub. No.: WO2013/102615
PCT Pub. Date: Jul. 11, 2013

(65) Prior Publication Data
US 2014/0366899 A1    Dec. 18, 2014

(30) Foreign Application Priority Data

Jan. 3, 2012 (EP) .................................... 12150114

(51) Int. Cl.
*A24F 47/00* (2006.01)
*A61M 15/06* (2006.01)
*A61M 11/04* (2006.01)

(52) U.S. Cl.
CPC ......... *A24F 47/008* (2013.01); *A61M 11/042* (2014.02); *A61M 15/06* (2013.01); *A61M 11/047* (2014.02); *A61M 2205/8206* (2013.01)

(58) Field of Classification Search
CPC ...................................................... A24F 47/008
(Continued)

(56) References Cited

U.S. PATENT DOCUMENTS 1,674,617 A    6/1928   De Benedictis
4,327,748 A *  5/1982   Divis ...................... A24F 13/02
                                                        131/187
(Continued)

FOREIGN PATENT DOCUMENTS

CN    1612406 A    5/2005
CN    2722943 Y    9/2005
(Continued)

OTHER PUBLICATIONS

Combined Chinese Office Action and Search Report issued Oct. 30, 2015 in Patent Application No. 201280069564.X (submitting English language translation only).

(Continued)

*Primary Examiner* — Eric Yaary
(74) *Attorney, Agent, or Firm* — Oblon, McClelland, Maier & Neustadt, L.L.P.

(57) ABSTRACT

There is provided an elongate aerosol-generating device having a polygonal transverse cross-section. The polygon includes at least six sides. The elongate aerosol-generating device includes a substrate receiving cavity configured to receive an aerosol-forming substrate, a heating element configured to heat an aerosol-forming substrate to generate an aerosol, and a power supply configured to provide power to the heating element. In addition, there is provided an aerosol-generating system, including the elongate aerosol-generating device, and a charging device including a cavity having a polygonal transverse cross-section corresponding to the polygonal transverse cross-section of the aerosol- (Continued)

generating device, the cavity being configured to receive the elongate aerosol-generating device.

9 Claims, 4 Drawing Sheets

(58) Field of Classification Search
USPC .................................................. 320/114–115
See application file for complete search history.

(56) References Cited

U.S. PATENT DOCUMENTS

| | | | | |
|---|---|---|---|---|
| 6,014,009 | A * | 1/2000 | Wierzbicki | H01M 2/1022 320/106 |
| 2006/0196518 | A1 | 9/2006 | Hon | |
| 2007/0247113 | A1 * | 10/2007 | Huang | H02J 7/0044 320/114 |
| 2008/0021072 | A1 | 1/2008 | Luzenberg | |
| 2010/0307518 | A1 * | 12/2010 | Wang | A24F 47/008 131/329 |
| 2010/0313901 | A1 | 12/2010 | Fernando et al. | |
| 2013/0019887 | A1 * | 1/2013 | Liu | A24F 47/008 131/329 |

FOREIGN PATENT DOCUMENTS

| | | |
|---|---|---|
| CN | 100381083 C | 4/2008 |
| CN | 201067079 Y | 6/2008 |
| CN | 201079011 Y | 7/2008 |
| CN | 101340981 A | 1/2009 |
| CN | 101862038 | 10/2010 |
| CN | 201833736 U | 5/2011 |
| FR | 2 354 720 | 1/1978 |
| GB | 741 101 | 11/1955 |
| GB | 2 301 040 | 11/1996 |
| JP | 2002-514910 A | 5/2002 |
| JP | 2006-524494 A | 11/2006 |
| KR | 10-2011-0079587 A | 7/2011 |
| TW | M292451 | 6/2006 |
| WO | WO 2011127644 A1 * 10/2011 ........... A24F 47/008 |  |

OTHER PUBLICATIONS

International Preliminary Report on Patentability and Written Opinion issued Jul. 17, 2014 in PCT/EP2012/077090.
International Search Report Issued Oct. 4, 2013 in PCT/EP12/077090 Filed Dec. 28, 2012.
Decision to Grant a Patent issued on Aug. 15. 2016 in Japanese Patent Application No. 2014-550693 (submitting English translation only).
Combined Chinese Office Action and Search Report issued Jun. 22, 2016 in Patent Application No. 201280069564.X submitting English translation only.
English translation only of Taiwanese Office Action dated Oct. 25, 2016 in corresponding Taiwan Patent Application No. 101150953, citing document AO therein (7 pages).
Office Action dated Apr. 7, 2016 in Korean Patent Application No. 10-2014-7018027 (with English language translation).

* cited by examiner

US 9,854,844 B2

POLYGONAL AEROSOL-GENERATING DEVICE AND SYSTEM

CROSS REFERENCE TO RELATED APPLICATION

This application is a national phase application based on PCT/EP2012/077090, filed on Dec. 28, 2012.

The specification relates to an aerosol-generating device with a polygonal cross-section. The specification also relates to a system comprising the aerosol-generating device and a charging device for receiving the aerosol-generating device.

Smoking articles in which an aerosol-forming substrate, such as a tobacco containing substrate, is heated rather than combusted are known in the art. The aim of such heated smoking articles is to reduce known harmful smoke constituents produced by the combustion and pyrolytic degradation of tobacco in conventional cigarettes. Typically in such heated smoking articles, an aerosol is generated by the transfer of heat from a heat source to a physically separate aerosol-forming substrate or material, which may be located within, around or downstream of the heat source. During smoking, volatile compounds are released from the aerosol-forming substrate by heat transfer from the heat source and entrained in air drawn through the smoking article. As the released compounds cool, they condense to form an aerosol that is inhaled by the consumer.

A number of prior art documents disclose aerosol-generating devices for consuming or smoking heated smoking articles. Such devices include, for example, heated smoking systems and electrically heated smoking systems.

It would be desirable to provide an aerosol-generating device that is capable of dissipating the excess heat generated by the device during use. It would also be desirable to provide such an aerosol-generating device that is ergonomic to hold in use. It would also be desirable to provide such a device that remains stationary while not in use.

It is also known in the art to provide a secondary device for charging the aerosol-generating device while the aerosol-generating device is not in use. Providing such a secondary charging device allows the aerosol-generating device to be smaller, and lighter. The secondary charging device may also provide means for storing information relating to the usage of the aerosol-generating device.

It would be desirable to provide an aerosol-generating system comprising an aerosol-generating device and a secondary device for charging the aerosol-generating device that reduces the possibility of incorrectly connecting the aerosol-generating device to the secondary device.

As used herein, an 'aerosol-generating device' relates to a device that interacts with an aerosol-forming substrate to generate an aerosol. The aerosol-forming substrate may be part of an aerosol-generating article, for example part of a smoking article. An aerosol-generating device may comprise one or more components used to supply energy from a power supply to an aerosol-forming substrate to generate an aerosol. For example, an aerosol-generating device may be a heated aerosol-generating device. An aerosol-generating device may be an electrically heated aerosol-generating device or a gas-heated aerosol-generating device. An aerosol-generating device may be a smoking device that interacts with an aerosol-forming substrate of an aerosol-generating article to generate an aerosol that is directly inhalable into a user's lungs thorough the user's mouth.

As used herein, the term 'aerosol-forming substrate' relates to a substrate capable of releasing volatile compounds that can form an aerosol. Such volatile compounds may be released by heating the aerosol-forming substrate. As an alternative to heating or combustion, in some cases volatile compounds may be released by a chemical reaction or by a mechanical stimulus, such as ultrasound. An aerosol-forming substrate may be solid or liquid or comprise both solid and liquid components. An aerosol-forming substrate may be adsorbed, coated, impregnated or otherwise loaded onto a carrier or support. An aerosol-forming substrate may conveniently be part of an aerosol-generating article or smoking article.

An aerosol-forming substrate may comprise nicotine. An aerosol-forming substrate may comprise tobacco, for example may comprise a tobacco-containing material containing volatile tobacco flavour compounds, which are released from the aerosol-forming substrate upon heating. In preferred embodiments an aerosol-forming substrate may comprise homogenised tobacco material, for example cast leaf tobacco. An aerosol-forming substrate may comprise at least one aerosol-former, such as propylene glycol or glycerine.

As used herein, the terms 'aerosol-generating article' and 'smoking article' refer to an article comprising an aerosol-forming substrate that is capable of releasing volatile compounds that can form an aerosol. For example, an aerosol-generating article may be a smoking article that generates an aerosol that is directly inhalable into a user's lungs through the user's mouth. An aerosol-generating article may be disposable.

Preferably an aerosol-generating article is a heated aerosol-generating article, which is an aerosol-generating article comprising an aerosol-forming substrate that is intended to be heated rather than combusted in order to release volatile compounds that can form an aerosol. The aerosol formed by heating the aerosol-forming substrate may contain fewer known harmful constituents than would be produced by combustion or pyrolytic degradation of the aerosol-forming substrate. An aerosol-generating article may be, or may comprise, a tobacco stick.

In one aspect there is provided an elongate aerosol-generating device having a polygonal transverse cross-section. The polygon comprises at least 6 sides.

By providing an aerosol-generating device with such a multi-faceted cross-section the surface area of the device is increased as compared to a device having a circular cross-section. Utilising a polygon with at least 6 sides advantageously provides a user with a more ergonomic feel, while increasing the surface area for heat dissipation.

In addition, providing a polygonal cross-section, with straight sides, advantageously increases the stability of the device when it is placed on a surface while it is not in use.

The polygon may comprise between 6 and 16 sides, preferably between 7 and 12 sides. In one preferred embodiment the polygon comprises 10 sides.

The polygon may be a regular polygon. The term regular polygon refers to a polygon that is equiangular, all of the angles are the same, and equilateral, all of the sides are the same length. The aerosol-generating device may have a regular polygonal transverse cross-section along its entire length. Alternatively, the aerosol-generating device may have a regular polygonal cross-section that extends along only a portion of its length. Where the regular polygonal cross-section does not extend along the entire length of the aerosol-generating device, for example, the cross-section of the aerosol-generating device may change due to a button, such as a button incorporated into the aerosol-generating device, such as a button adapted to activate the device in use.

As used herein, the term "length" refers to the dimension in the longitudinal direction. The term "longitudinal" refers to the main axis of the elongate aerosol-generating device. As used herein, the term "transverse" refers to a direction perpendicular to the longitudinal direction.

At least one end of the aerosol-generating device may be tapered. Alternatively, both ends of the aerosol-generating device may be tapered. Preferably, the radius of the or each end face of the tapered end is at least 50% of the maximum radius of the aerosol-generating device. The radius of a polygon is measured from the centroid of the polygon to a vertex thereof.

Where the at least one end of the aerosol-generating device is tapered, preferably, the at least one end of the aerosol-generating device is tapered along at least about 5% of the length of the device. More preferably, the at least one end of the aerosol-generating device is tapered along at least about 7% of the length of the device. Yet more preferably, the at least one end of the aerosol-generating device is tapered along at least about 7.5%.

Where the at least one end of the aerosol-generating device is tapered, the taper may be linear or curved.

Preferably, the elongate aerosol-generating device comprises an outer housing having a substrate receiving cavity adapted to receive an aerosol-forming substrate, a heating element adapted to heat an aerosol-forming substrate to generate an aerosol, and a power supply adapted to provide power to the heating element. The device may also comprise a controller for controlling the power supplied from the power supply to the heating element.

Where the aerosol-generating device comprises a substrate receiving cavity, a holder may be provided within the cavity. The holder is adapted to hold an aerosol-forming substrate adjacent the end of the aerosol-generating device having the cavity. A plurality of air inlets to a plurality of air channels within the device may be formed the holder and the outer housing portion. The air channels may diverge away from the air inlets within the device as the outer housing diverges with the tapering. Providing such air channels may improve the air entrainment within the device. In addition, the entrained air may improve the insulation between the aerosol-forming substrate and the outer housing.

The substrate receiving cavity may be adapted to receive a smoking article comprising an aerosol-forming substrate having a mouth end and a distal end, the aerosol-forming substrate being at the distal end.

In use, a user applies his or her lips to the mouth end of the smoking article and inhales while activating the device. Air and any aerosol-generated within the device are drawn through the mouth end of the smoking article to be inhaled by the user. When the user inhales, air and aerosol move through the smoking article from the distal end to the mouth end. In some embodiments, air may be drawn into the device through the end of the device proximal to the smoking article. In some embodiments, air may be drawn into the device through a sidewall. In other embodiments, air may be drawn into the device through a combination of the proximal end of the device and a sidewall of the device.

The smoking article may be substantially cylindrical in shape. The smoking article may be substantially elongate. The smoking article may also have a length and a circumference substantially perpendicular to the length. The smoking article substrate may be received in the cavity of the aerosol-generating device such that the length of the smoking article is substantially parallel to the airflow direction in the aerosol-generating device.

The outer housing of the aerosol-generating device may be manufactured from two, four or more portions. The portions are preferably joined together along a transverse cross-section of the device, and may be adapted to join around a button on the device. Where the outer housing comprises four portions, the portions may be two tapered end portions, and two substantially cylindrical central portions. The outer housing of the aerosol-generating system may be manufactured from any suitable material or combination of materials. Examples of suitable materials include, but are not limited to, metals, alloys, plastics or composite materials containing one or more of those materials, or thermoplastics that are suitable for food or pharmaceutical applications, for example polypropylene, polyetheretherketone (PEEK) and polyethylene.

In a further aspect, there is also provided an aerosol-generating system. The system comprises an elongate aerosol-generating device as described above, and a charging device comprising a cavity having a polygonal transverse cross-section corresponding to the polygonal transverse cross-section of the aerosol-generating device, the cavity being adapted to receive the elongate aerosol-generating device.

Preferably, the aerosol-generating device receiving cavity comprises means for keying the aerosol-generating device to the charging device. The keying means may comprise at least one notch for receiving at least one corresponding protrusion on the aerosol-generating device. The at least one protrusion may be a button adapted to activate the aerosol-generating device.

In one embodiment where the aerosol-generating device comprises at least one tapered end, the tapered end enables the device to be more easily inserted into the cavity of the charging device.

As used herein, means plus function features may be expressed alternatively in terms of their corresponding structure.

Any feature relating to one aspect may be applied to other aspects, in any appropriate combination. In particular, method aspects may be applied to apparatus aspects, and vice versa. Furthermore, any, some or all features in one aspect can be applied to any, some or all features in any other aspect, in any appropriate combination.

It should also be appreciated that particular combinations of the various features described and defined in any aspects of the invention can be implemented or supplied or used independently.

These and other aspects of the apparatus will become apparent from the following exemplary embodiments that are described with reference to the following figures in which.

Figure 1:
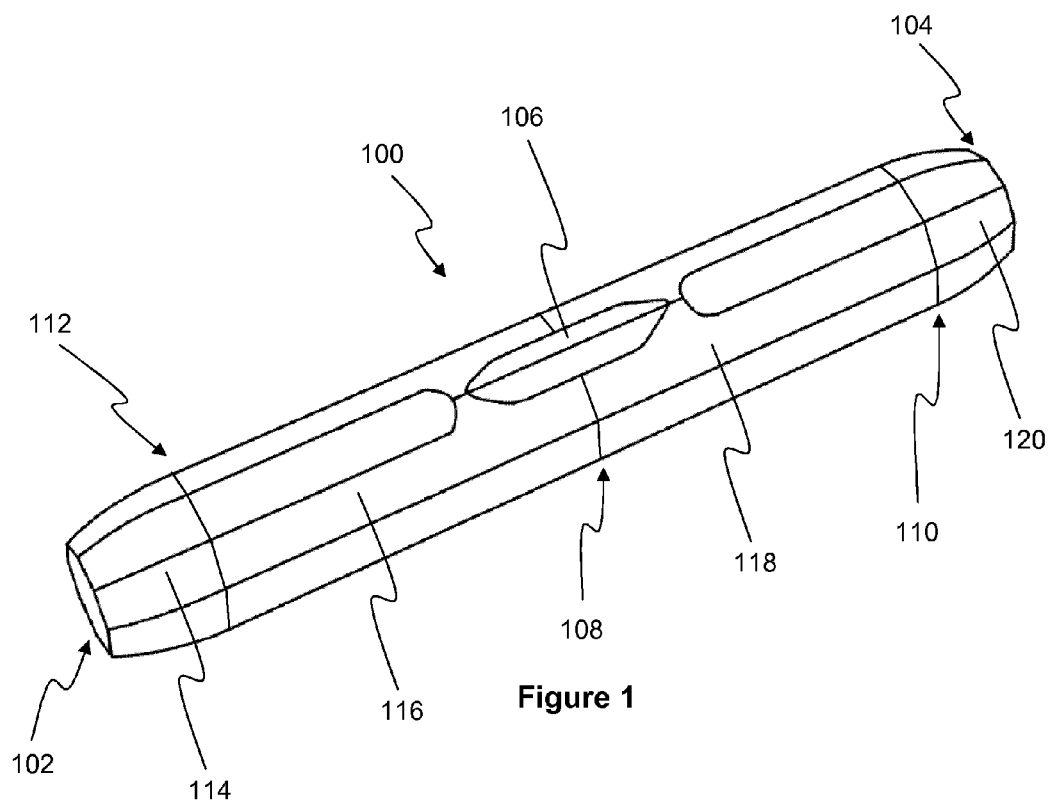
FIG. 1 shows a perspective view of one embodiment of an aerosol-generating device.
Figure 2:
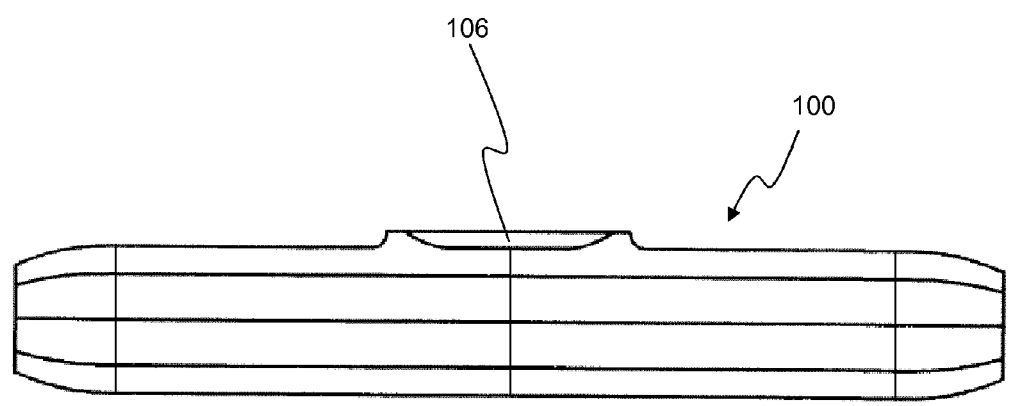
FIG. 2 shows a side-view of the aerosol-generating device shown in FIG. 1.
Figure 3A:
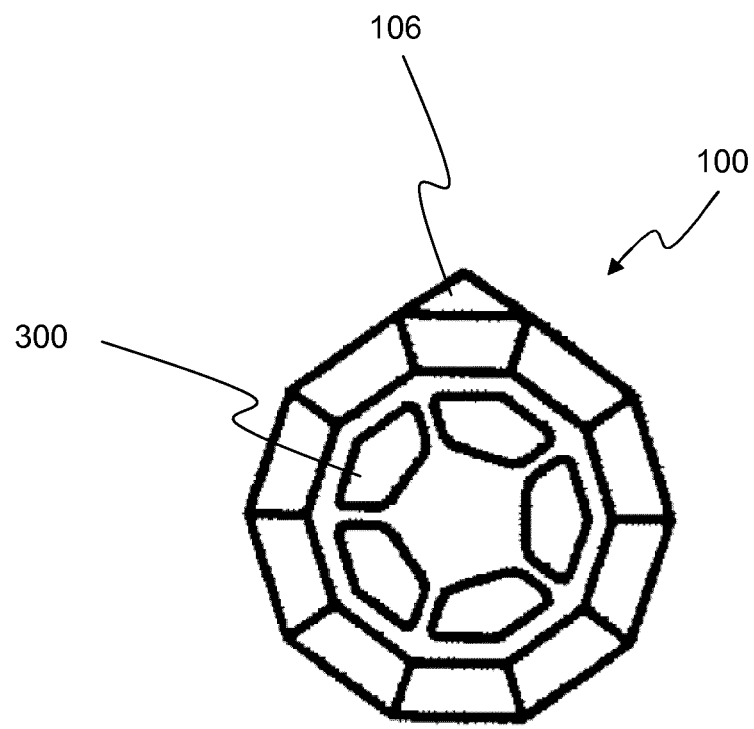
Figure 3B:
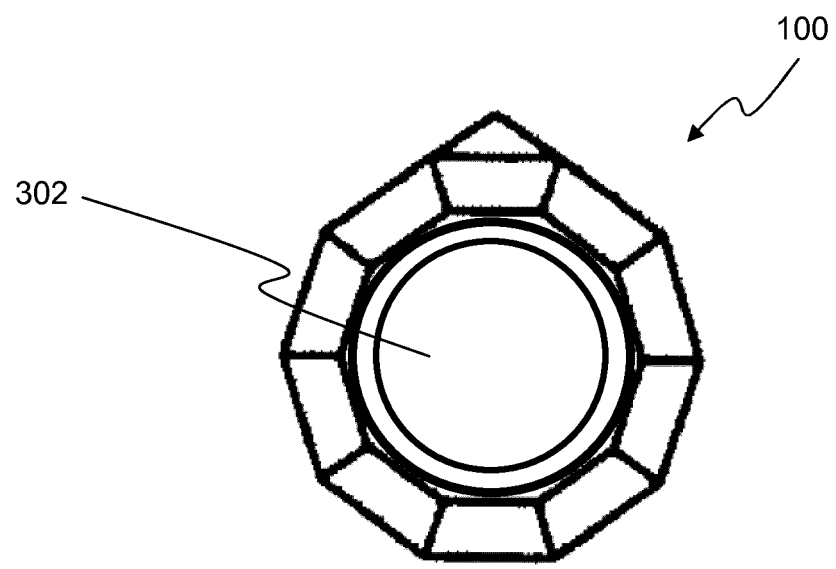
Figure 4:
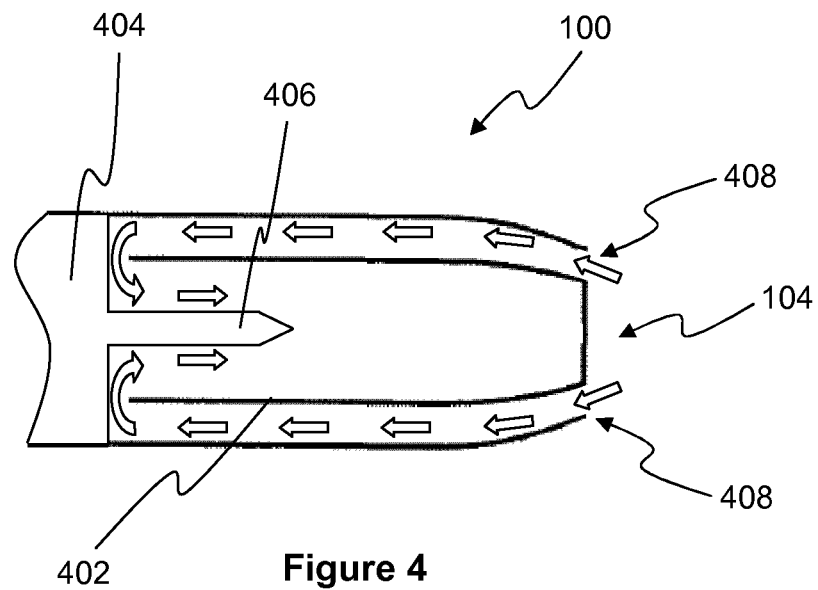
Figure 6:
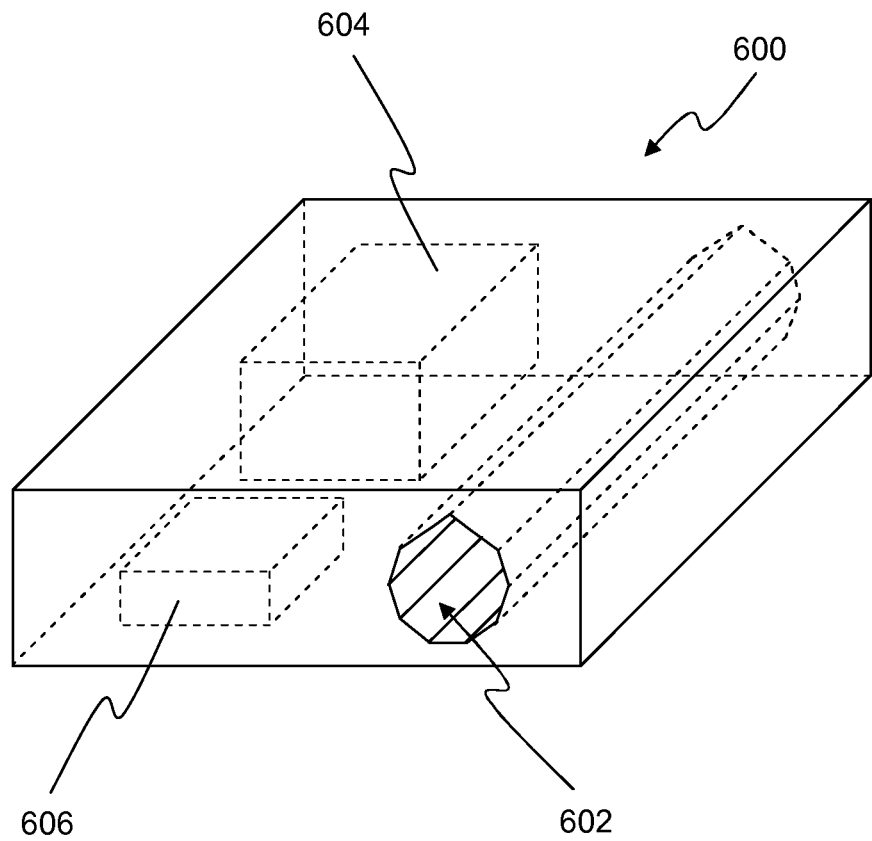
Figure 5:
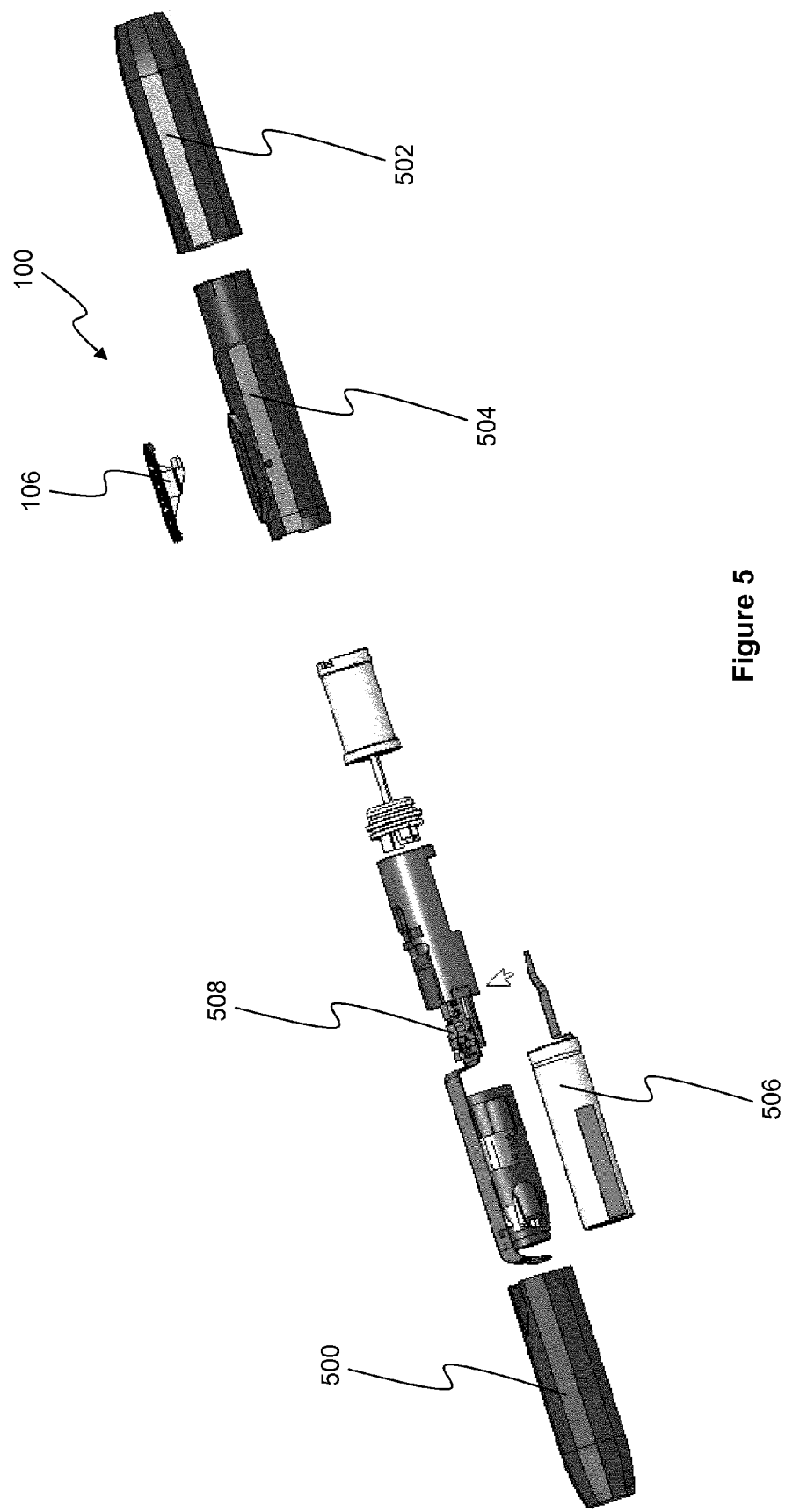

FIGS. 3(*a*) and 3(*b*) show end-views of the aerosol-generating device shown in FIGS. 1 and 2;

FIG. 4 shows a schematic diagram of the air flow through the aerosol-generating device shown in FIGS. 1, 2 and 3;

FIG. 5 shows an exploded view of the aerosol-generating device shown in FIGS. 1, 2 and 3; and FIG. 6 shows a perspective view of a charging device adapted to receive and charge the aerosol-generating device shown in FIGS. 1 to 5.

FIG. 1 shows a perspective view of one embodiment of an aerosol-generating device 100. The device 100 is elongate and comprises two opposed polygonal end faces 102 and 104 respectively. The device 100 also comprises a button 106 adapted to activate the aerosol-generating device when pressed. The operation of the device is described in further detail below. As can be seen, the outer housing of the device 100 comprises four portions joined at the coupling lines 108, 110 and 112 respectively. The four portions respectively are a first tapered end portion 114 attached to a first central portion 116, a second tapered end portion 120 attached to a second central portion 118. The four portions fit together around an inner housing (not shown) in a manner described below.

The device 100 has a regular polygonal cross-section along the majority of its length. However, in the region of the button 106 the cross-section is no longer a regular polygon, but remains a simple polygon.

FIG. 2 shows a side-view of the aerosol-generating device 100 shown in FIG. 1. As can be seen, the button 106 protrudes from the surface of the device so that the user may more easily push the button to activate the device in use.

FIGS. 3(a) and 3(b) show the polygonal end faces 102 and 104 of the device 100 respectively. As can be seen, the polygon in this embodiment has 10 sides. The button 106 has a triangular cross-section. FIG. 3(a) shows the end face 102 with five electrical connections 300. The electrical connections are adapted to connect with a secondary, charging, device which is described in further detail below. As can be seen, providing a polygonal cross-section allows for the five electrical connections 300 to more easily be positioned on the end face 102 of the aerosol-generating device 100. FIG. 3(b) shows the end face 104. A cavity 302 is provided to accept a smoking article comprising an aerosol-forming substrate.

FIG. 4 shows a schematic representation of the air flow through the device. As can be seen in this embodiment, when the smoking article is received within the cavity 302 of the device 100, air drawn into the device passes around the outside of a smoking article holder 402 having a circular cross-section. The drawn air proceeds into the aerosol-forming substrate at the distal end of the smoking article adjacent a heating bushing 404 of a blade shaped heating element 406 provided in the cavity 302. The drawn air proceeds through the substrate, entraining the aerosol, and then to the mouth end of the smoking article. Air inlets 408 formed between the outer housing and the holder 402 enable air to be entrained more efficiently and aid with insulating the heated smoking article from the outer housing. The air inlets 408 may be seen in cross-section in FIG. 3(b).

FIG. 5 shows an exploded view of the aerosol-generating device 100. The device comprises a first outer housing portion 500 comprising the first tapered end portion 114 and the first central portion 116. The device further comprises a second outer housing portion 502 comprising the second tapered end portion 120 and the second central portion 118. The device also comprises an inner housing 504. The device also comprises a power supply in the form of a battery 506, a controller 508 adapted to control the power supplied from the battery 506 to a heating element (not shown). The button 106 is located in the central housing portion 504, and engages with the controller 508 to enable the user to activate the device.

In use, a user inserts a smoking article comprising an aerosol-forming substrate into the cavity 302 of the aerosol-generating device 100. The aerosol-forming substrate engages with the heating element 406. When the user activates the device by pushing button 106, power is supplied to the heating element 406 from the battery 506 via the controller 508. The heating element 406 heats the aerosol-forming substrate to generate an aerosol and the aerosol is entrained within the air flow as the user draws on the mouth end of the smoking article.

FIG. 6 shows a perspective view of a charging device 600 adapted to receive and charge the aerosol-generating device 100. The charging device comprises a cavity 602 adapted to receive the aerosol-generating device 100, a power supply in the form of a battery 604, and a controller 606. When the device 100 requires charging it is inserted into the cavity 602, and the electrical connections 300 are coupled to corresponding electrical connections (not shown) at the bottom of the cavity 602.

The cavity 602 has a polygonal cross-section that corresponds to the cross-section of the aerosol-generating device 100. In addition, the cavity is provided with an additional notch that allows the button 106 of the device to be located within the cavity 602. The notch and button protrusion on the device 100 allow the device to be keyed to the charging device 600 such that the device 100 may only be inserted into the charging device 600 in one orientation. By providing such a keying means, the user is prevented from inserting the device 100 incorrectly, and thus the correct electrical connections are made every time the device 100 is inserted. In addition, the tapered end portion 114 of the aerosol-generating device 100 allows the user to more easily insert the device into the cavity 602.

It is of course to be understood that the specification is not intended to be restricted to the details of the above embodiments which are described by way of example only.

The invention claimed is:

1. An aerosol-generating system, comprising:
an elongate aerosol-generating device having a polygonal transverse cross-section, wherein the polygon comprises at least six sides; and
a charging device comprising a cavity having a polygonal transverse cross-section corresponding to the polygonal transverse cross-section of the aerosol-generating device, the cavity being configured to receive the elongate aerosol-generating device and comprising means for keying the elongate aerosol-generating device to the charging device,
wherein the means for keying comprises at least one notch configured to receive at least one corresponding protrusion on the elongate aerosol-generating device, and
wherein the at least one protrusion is a button configured to activate the elongate aerosol-generating device.

2. The aerosol-generating system according to claim 1, wherein the polygon comprises between seven and twelve sides.

3. The aerosol-generating system according to claim 1, wherein the polygon is a regular polygon.

4. The aerosol-generating system according to claim 1, wherein at least one end of the elongate aerosol-generating device is tapered.

5. The aerosol-generating system according to claim 1, wherein both ends of the elongate aerosol-generating device are tapered.

6. The aerosol-generating system according to claim 4, wherein a radius of an end face of the elongate aerosol-generating device or said at least one end is at least 50% of a maximum radius of the elongate aerosol-generating device.

7. The aerosol-generating system according to claim 4, wherein said at least one end of the elongate aerosol-generating device is tapered along at least 5% of a length of the device.

8. The aerosol-generating system according to claim 4, wherein the taper is linear or curved.

9. The aerosol-generating system according to claim 1, the elongate aerosol-generating device further comprising:
- a substrate receiving cavity configured to receive an aerosol-forming substrate;
- a heating element configured to heat the aerosol-forming substrate to generate an aerosol; and
- a power supply configured to provide power to the heating element.

\* \* \* \* \*